United States Patent
Bettenga et al.

(10) Patent No.: US 12,102,315 B2
(45) Date of Patent: Oct. 1, 2024

(54) METHODS FOR PASSING A POSTERIOR BUTTON SUTURE FOR MEDICAL PROCEDURES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Mason Bettenga, Memphis, TN (US); Pascal Boileau, Nice (FR)

(73) Assignees: Smith & Nephew, Inc., Memphis, TN (US); Smith & Nephew Orthopaedics AG (CH); Smith & Nephew Asia Pacific Pte. Limited, Singapore (SG)

( * ) Notice: Subject to any disclaimer, the term of this patent is extended or adjusted under 35 U.S.C. 154(b) by 1004 days.

(21) Appl. No.: 17/052,393

(22) PCT Filed: May 1, 2019

(86) PCT No.: PCT/US2019/030275
§ 371 (c)(1),
(2) Date: Nov. 2, 2020

(87) PCT Pub. No.: WO2019/213317
PCT Pub. Date: Nov. 7, 2019

(65) Prior Publication Data
US 2021/0085309 A1    Mar. 25, 2021

Related U.S. Application Data

(60) Provisional application No. 62/665,684, filed on May 2, 2018.

(51) Int. Cl.
*A61B 17/04*        (2006.01)

(52) U.S. Cl.
CPC ...... *A61B 17/0401* (2013.01); *A61B 17/0482* (2013.01); *A61B 17/0485* (2013.01);
(Continued)

(58) Field of Classification Search
CPC ............ A61B 17/0401; A61B 17/0482; A61B 17/0485; A61B 2017/0404; A61B 2017/0409; A61F 2/40; A61F 2/4081
See application file for complete search history.

(56) References Cited

U.S. PATENT DOCUMENTS

| 2008/0086147 A1* | 4/2008 | Knapp | A61B 17/0485 |
| | | | 606/113 |
| 2013/0304120 A1* | 11/2013 | Stone | A61B 17/0401 |
| | | | 606/232 |
| 2017/0112625 A1* | 4/2017 | Taverna | A61B 17/1778 |

OTHER PUBLICATIONS

Defintion of "pin". Merriam Webster Dictionary. 2009. https://www.merriam-webster.com/dictionary/pin.*

* cited by examiner

*Primary Examiner* — Ariana Zimbouski
*Assistant Examiner* — Mikail A Mannan
(74) *Attorney, Agent, or Firm* — ArentFox Schiff LLP; Joseph M. Maraia; Marlo Schepper Grolnic

(57) ABSTRACT

Methods for suspension fixation most applicable for a Latarjet of bone block procedure are performed using an open surgery with an anterior approach. The method passes endobuttons and sutures through the glenoid from posterior without the need of a posterior drill guide and disposable drill/sleeve. As an alternative embodiment, a passing pin with a slot at the advancing end may be used to further reduce surgical steps. The passing pin may be advanced and exit the muscle, and the suture loop may be directly attached to the pin rather than a secondary shuttle suture and then retrieved anteriorly.

8 Claims, 4 Drawing Sheets

(52) U.S. Cl.
CPC ................ *A61B 2017/0404* (2013.01); *A61B 2017/0409* (2013.01)

METHODS FOR PASSING A POSTERIOR BUTTON SUTURE FOR MEDICAL PROCEDURES

CROSS-REFERENCE TO RELATED APPLICATIONS

This application is the U.S. national phase entry under 35 U.S.C. § 371 of International Application No. PCT/US19/30275, filed May 1, 2019, entitled "METHODS FOR PASSING A POSTERIOR BUTTON SUTURE FOR MEDICAL PROCEDURES", which in turn claims priority to and benefit of U.S. Provisional Application No. 62/665,684, filed May 2, 2018, entitled "METHODS FOR PASSING A POSTERIOR BUTTON SUTURE FOR MEDICAL PROCEDURES", the contents of which are incorporated herein by reference in their entirety for all purposes.

FIELD

This disclosure relates to methods for passing a posterior button suture for medical procedures. In particular, this disclosure relates to methods for passing endobuttons and sutures, for example, through the glenoid during a Latarjet or bone block procedure.

BACKGROUND

The shoulder joint, also referred to as the glenohumeral joint, is the joint between the glenoid cavity (a part of the scapula) and the head of the humerus (upper arm bone). The glenoid cavity is shallow, covering only about a third of the head humeral head. As a result, the glenoid cavity provides relatively little bony constraint upon motion of the humerus and the glenohumeral joint exhibits the widest range of motion of all joints in the human body. While the glenohumeral joint is also constrained by soft tissue (e.g., cartilage attached to the rim of the glenoid cavity, tendons, etc.), soft tissue in general cannot provide the same degree of constraint as bone. Accordingly, it is relatively easy to force the humerus from its normal anatomical position with respect to the glenoid socket, that is, to dislocate the shoulder. While not life threatening, a dislocated shoulder can cause pain and immobilization of the joint, impacting a patient's lifestyle.

In the case of severe bone loss caused by shoulder instability and/or dislocation, a surgeon may perform a bone block procedure such as a "Latarjet procedure" to make the repair. In a Latarjet procedure, a surgeon attempts to restore bone mass to the glenoid cavity by securing a bone graft to the surface of the glenoid suffering bone loss. The bone graft is typically harvested from the iliac crest, shaped, and screwed to the front of the socket. The bone graft may or may not be attached to soft tissue. The bone graft is commonly placed outside the capsule of the shoulder so that the bone graft does not rub directly on the cartilage of the humeral head. When successful, the bone graft acts as a scaffold, allowing the glenoid bone to grow into the bone graft and restore the lost glenoid bone mass. Risk of recurrent dislocation is low following a Latarjet procedure.

During the Latarjet procedure, fixation devices, such as solid screws, may be used to provide compression when securing the graft to the bone. Alternatively, if suspension fixation is desired, the fixation devices may be in the form of a flat button that is positioned on a surface of the bone graft and/or bone and is tensioned in place by a suture. Traditional Latarjet or bone block procedures also utilizes posterior portals. Shuttling endobuttons from the posterior in a current Latarjet or bone block procedure requires the use of costly and bulky posterior glenoid drill guides and disposable drills/sleeves.

SUMMARY

Described herein is a method for suspension fixation most applicable for a Latarjet of bone block procedure performed using an open surgery with an anterior approach. The method of this disclosure passes endobuttons and sutures through the glenoid from posterior without the need of a posterior drill guide and disposable drill/sleeve. Removing the need of a posterior drill guide and disposable drill/sleeve decreases the number of surgical tools required for a procedure, which, in turn, decreases risk for surgical site infection and post-surgical patient complications. Since the drilling of the glenoid is controlled from the anterior exposure, this method is a fast and easy way of shuttling the sutures from back to front. As an alternative embodiment, a passing pin with a slot at the advancing end may be used to further reduce surgical steps. The passing pin may be advanced and exit the muscle, and the suture loop may be directly attached to the pin rather than a secondary shuttle suture and then retrieved anteriorly.

In embodiments, the method of this disclosure includes drilling a hole through a glenoid from an anterior side of the glenoid via an anterior portal. A pin is passed through the hole in the glenoid via the anterior portal and out past a posterior side of the glenoid. A distal end of the pin is then secured relative to a flexible member attached to a posterior fixation member. The pin is retrieved anteriorly so as to pass the flexible member through the hole in the glenoid and draw the posterior fixation member into contact with the posterior side of the glenoid. A graft or implant is then secured to an anterior side of the glenoid via suspension fixation between the posterior fixation member and an anterior fixation member.

In embodiments, the posterior fixation member includes a first post, the anterior fixation member includes a second post, and a diameter of the hole is substantially equal to a diameter of the first or second post. In some instances, the pin further includes an advancing end and a slot at the advancing end. In some examples, the method further includes drilling a second hole to provide a second point of fixation. In instances, the method further includes tying a surgical knot in the flexible member, the flexible member being a suture. In examples, a suture loop of the suture is attached to the pin.

Additionally, described herein is an alternative method for suspension fixation of a graft or implant. The method includes drilling a hole through a glenoid from an anterior side of the glenoid via an anterior portal. A first end of a shuttle suture is passed through the hole in the glenoid via the anterior portal and out past a posterior side of the glenoid. The first end of the shuttle suture is secured relative to a flexible member attached to a posterior fixation member. The shuttle suture is then retrieved anteriorly so as to pass the flexible member through the hole in the glenoid and draw the posterior fixation member into contact with the posterior side of the glenoid. The graft or implant is then secured to an anterior side of the glenoid via suspension fixation between the posterior fixation member and an anterior fixation member.

In embodiments, the posterior fixation member includes a first post, the anterior fixation member includes a second post, and a diameter of the hole is substantially equal to a diameter of the first or second post. In instances, the method further includes tying a surgical knot in the flexible member, the flexible member being a suture. In some examples, the method further includes using a secondary shuttle suture with a suture loop attached to provide suspension fixation between the posterior fixation member and an anterior fixation member.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1:
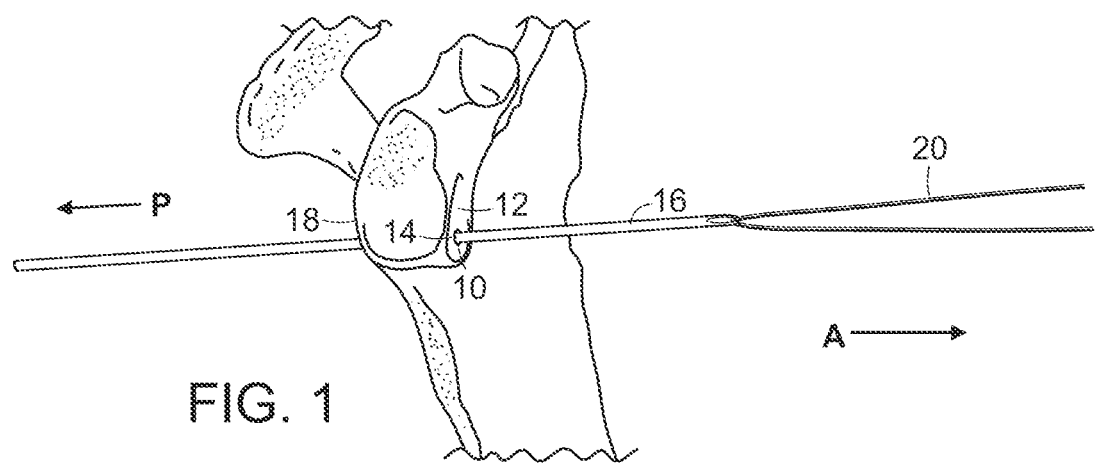
FIG. 1 illustrates a view of a method of suspension fixation where a hole 10 is drilled from an anterior of a glenoid 12 and a pin 16 and a flexible member 20, e.g. shuttle suture, are advanced from the anterior out a back of a deltoid (deltoid not shown)

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts. The posterior direction is denoted by arrow "P" in FIGS. 1-8. The anterior direction is denoted by arrow "A" in FIGS. 1-8.

Figure 2:
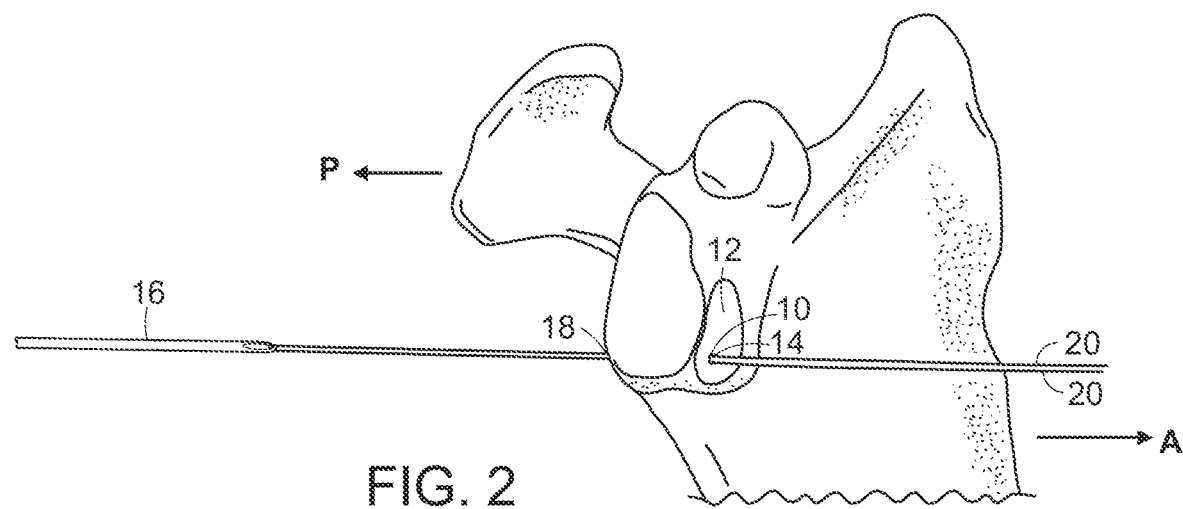
FIG. 2 illustrates a view of a method of suspension fixation in FIG. 1 with the pin 16 advanced completely from the anterior out a back of a deltoid.

FIG. 1 and FIG. 2 illustrate two views of a fixation method where a pin 16 is advanced through a hole 10 in the glenoid 12 from an anterior portal 14 and out past a posterior side 18 of the glenoid 12, according to the present disclosure. FIG. 1 illustrates partial advancement of the pin 16 in the posterior direction that is denoted by arrow "P". The pin 16 may be composed of metal, injection molded plastic, or an assortment of other alternative materials A flexible member 20 is also illustrated in FIG. 1 threaded through or otherwise coupled to pin 16. FIG. 2 is similar to FIG. 1 and illustrates full advancement of the pin 16 through the hole 10 in the glenoid 12.

Figure 3:
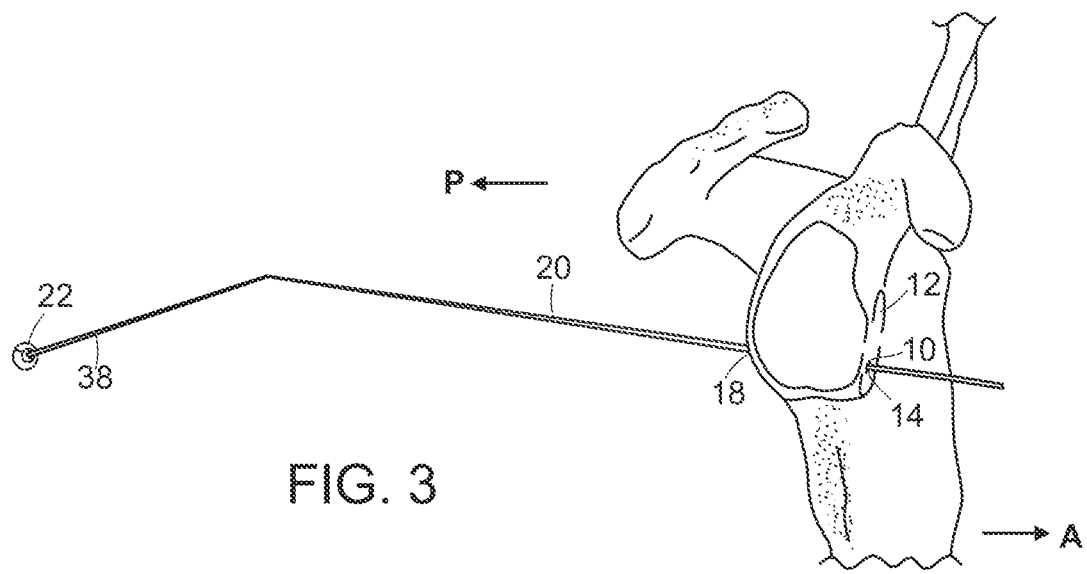
FIG. 3 illustrates a view of a method of suspension fixation where a posterior fixation member 22, e.g. an endobutton, and a suture loop are connected to the flexible member, e.g. shuttle suture, and positioned for anterior retrieval.
Figure 4:
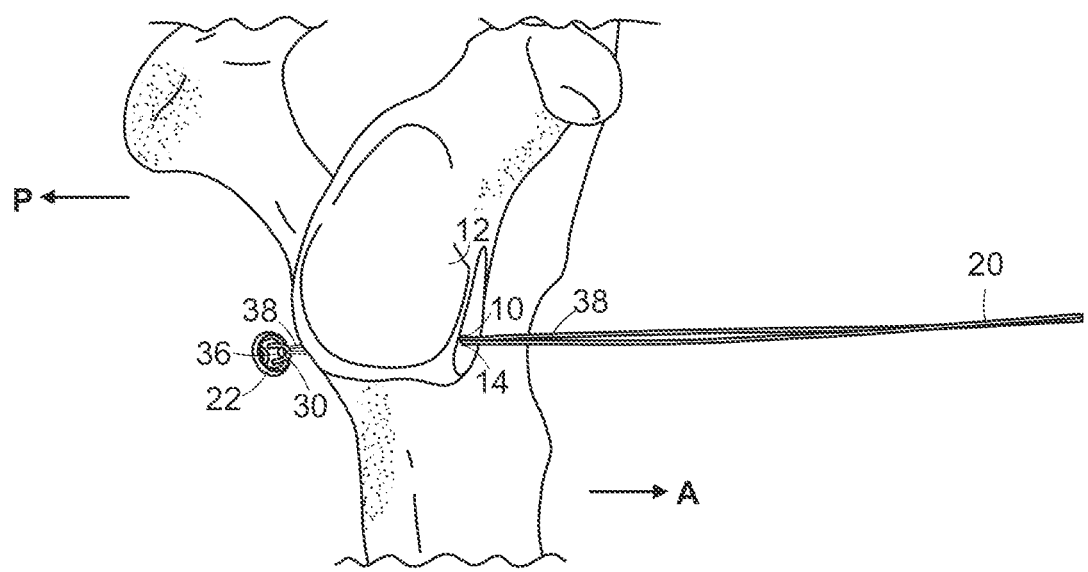
FIG. 4 illustrates a view of a method of suspension fixation where a posterior fixation member 22, e.g. an endobutton, and a suture loop 38 are coupled to a flexible member 20, e.g. a suture or a shuttle suture, and are retrieved anteriorly through the glenoid 12 of a patient's shoulder.

FIG. 3 illustrates a method of suspension fixation where a posterior fixation member 22. e.g. an endobutton, and a suture loop 38 are coupled to a flexible member 20, e.g. shuttle suture, and then positioned to be retrieved anteriorly through the hole 10 of the glenoid 12 of a patient's shoulder. A pin 16 (not shown) coupled to the flexible member 20 may be used to assist in anterior retrieval, where the anterior movement of pin 16 from posterior side 18 to the anterior portal 14 is denoted by arrow "A" FIG. 4 illustrates a view of a method of suspension fixation where a posterior fixation member 22, e.g. an endobutton, and a suture loop 38 are coupled to a flexible member 20, e.g. a suture or a shuttle suture, and are retrieved anteriorly through the glenoid 12 of a patient's shoulder. In FIG. 4, fixation member 22 has a post 30 through which a suture loop 38, which may be a component of flexible member 20, and/or the flexible member 20 are coupled. In FIG. 4, post 30 includes an eyelet 36 through which the suture loop 38, which may be a component of flexible member 20, and/or the flexible member 20 are coupled.

Figure 5:
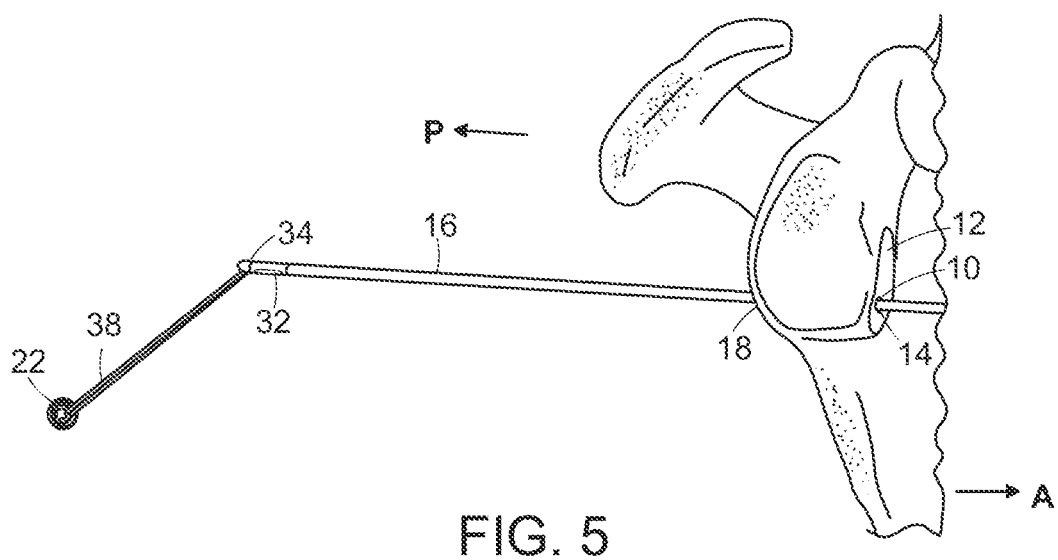
FIG. 5 illustrates an embodiment of a method of suspension fixation where the pin 16 has a slot at the advancing end used to further reduce surgical steps.

FIG. 5 illustrates an embodiment of a method of suspension fixation where the pin 16 has a slot 32 at the advancing end 34 to further reduce surgical steps. The pin 16 can be advanced to exit the muscle, and the suture loop 38, which may be a primary flexible member, can be directly attached to the pin 16 rather than a secondary flexible member 20, e.g. shuttle suture. In the aforementioned system, the passing pin 16 and suture loop 38 are retrieved anteriorly. To perform the method of fixation described herein, the pin 16 first advances from the anterior of the glenoid 12 to the posterior of the glenoid 12. In other words, the pin 16 first advances in the posterior direction. A posterior fixation member 22 is then added and pin 16 is advanced from the posterior of the glenoid 12 to the anterior of the glenoid 12. In other words, the pin 16 secondarily advances in the anterior direction.

Figure 6:
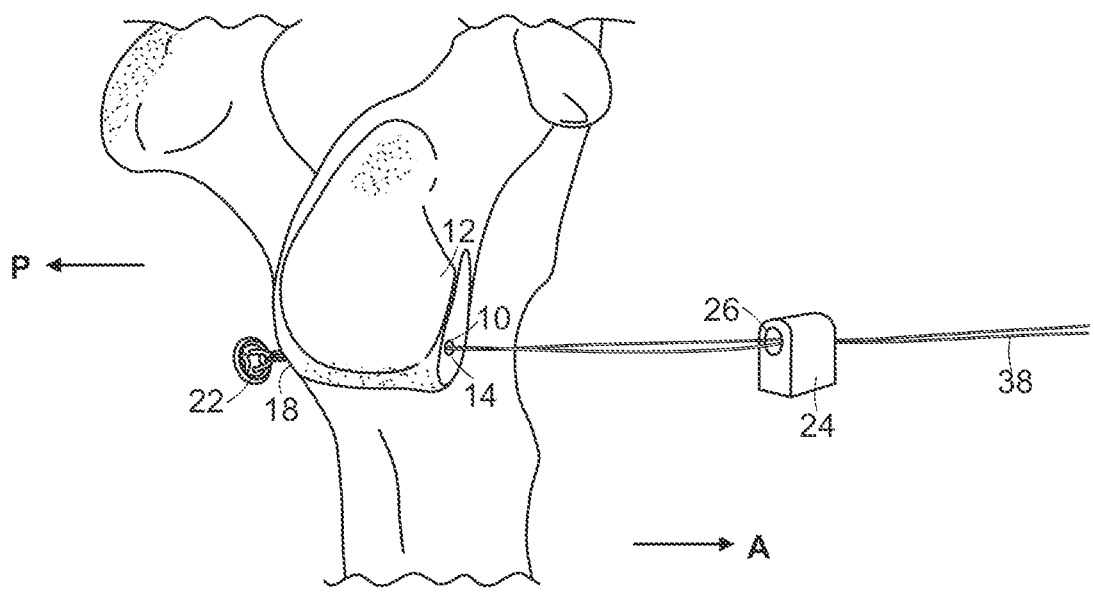
FIG. 6 illustrates a view of a method of suspension fixation where the graft 24 is secured to an anterior side of the glenoid 12.
Figure 7:
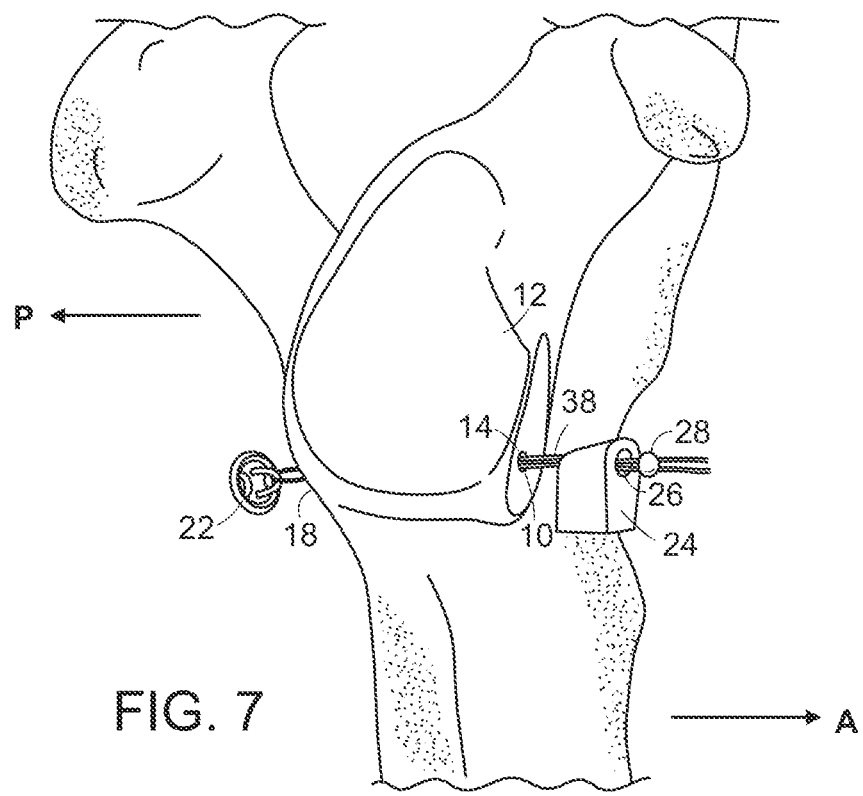
FIG. 7 illustrates a view of a method of suspension fixation where the graft 24 is secured via suspension fixation between the posterior fixation member 22 and an anterior fixation member 28, e.g. a suture knot.

FIG. 6 illustrates a method of suspension fixation where the graft 24 is secured to an anterior side of the glenoid 12. FIG. 7 illustrates a method of suspension fixation where the graft 24 is secured via suspension fixation between the posterior fixation member 22 and an anterior fixation member 28, e.g. a suture knot. Beneficially, a post 30 of the posterior fixation member 22 and/or anterior fixation member 28 provides greater or equal shear support to the fixation member 22, 28 across the fracture line of the bone of the glenoid 12 as compared to surgical screws. In one example, the fixation member 22, 28 has a post and a diameter of the post is selected to be substantially equal to the diameter of the hole 10, which may be about 2.8 mm.

Furthermore, when two or more fixation members 22, 28 are used, the fixation members 22, 28 additionally provide rotational stability to the graft 24 with respect to the underlying bone.

Absorbable materials, non-absorbable materials, or a combination of the aforementioned materials may be used as fixation members (e.g. anterior 28 and/or posterior 22 fixation members). A polymer such as polylactic acid may be preferred as an absorbable material for its slower absorption rate and therefore longer retention of structural integrity.

In examples, the bone graft 24 may be a coracoid bone graft, an iliac crest bone graft or an allograft. After hole(s) 10 are formed in the glenoid 12, the patient's shoulder is prepared for insertion of the fixation member 22. Non-limiting examples of methods for preparing a patient's shoulder are described in U.S. Patent Publication No. 2014-0277185 (Boileau et al.), incorporated herein by reference. An ancillary fastener 28, such as a round button, may be the fixation member 28 or a component of the fixation member 28. The ancillary fastener 28 may be pre-attached to a flexible member 38, e.g. a tension suture. Non-limiting examples of ancillary fasteners 28 are described in U.S. Patent Publication No. 2012/0310279 (Sikora et al), U.S. Patent Publication No. 2014-0277185 (Boileau et al.), and in the Endobutton family of products (manufactured by Smith & Nephew, Inc., Andover, MA, USA), incorporated herein by reference. The flexible member 38 is slidably passed through an opening in the ancillary fastener 28, or otherwise coupled to the ancillary fastener 28, such that the distance between the ancillary fastener 28 and the fixation member 22 can be adjusted by pulling on the ends of the flexible member 38. The ends of the flexible member 38 are pulled, for example by a shuttle suture 20 through the hole(s) 10 in the patient's glenoid 12 and hole(s) 26 in the patient's graft 24, until the ancillary fastener 28 is positioned below the glenoid 12 and the ends of the flexible member 38 extend from the hole(s) 26 in the graft 24. A width of the hole 10 through the glenoid 12 may be about 3.8 mm and a width of the hole or passage 26 through the graft 24, e.g. bone graft, may be about 2.5 mm.

Figure 8:
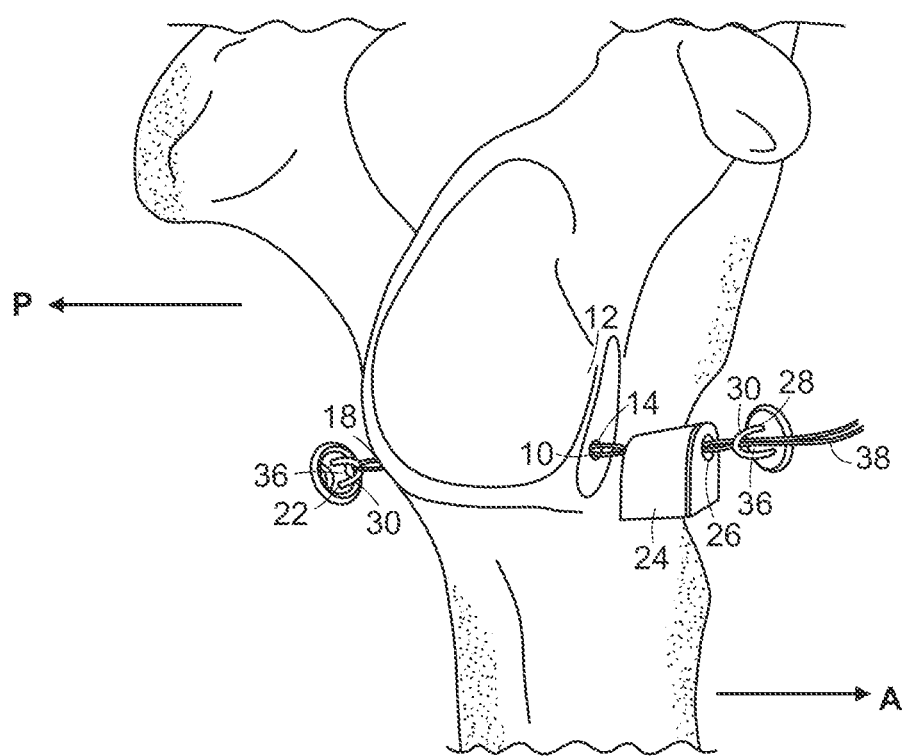
FIG. 8 illustrates a view of a method of suspension fixation where the graft 24 is secured via suspension fixation between the posterior fixation member 22 and an anterior fixation member 28, e.g. an endobutton. Specifically, FIG. 8 displays the point where the graft 24 and an anterior fixation member 28, e.g. an endobutton, are loaded to complete the reduction.

FIG. 8 illustrates a view of a method of suspension fixation where the graft 24 is secured via suspension fixation between the posterior fixation member 22 and an anterior fixation member 28, e.g. an endobutton. Specifically, FIG. 8 displays the point where the graft 24 and an anterior fixation member 28, e.g. an endobutton, are loaded to complete the reduction. The same procedure as described above and further detailed below can be used to create a second point of suspension fixation, if desired. While only one hole 10 is shown in FIGS. 1-8, one or more holes 10 (and thus one or more posterior fixation members 22) may be used in the method for suspension fixation. The flexible member that interacts with or attaches to the fixation member 22 may be a suture 20, e.g. a lead or pull suture. In some instances, the post 30 of the fixation member 22 includes an eyelet 36 extending through the distal end of the post 30 for passage of the flexible member 20. Where the flexible member 38 is a tension suture, the tension suture 38 may be slidably coupled to the eyelet 36. Sizes of the eyelets are variable, and are selected based on the size of the suture used. The form of the flexible member 38 may be varied, in certain examples. For example, the flexible member 38, e.g. a tension suture, may be formed in a suture loop or bundle. In further examples, the flexible member 38 may be formed from a high-strength polyethylene or may be formed from metallic wire.

Since passage 26 of the bone graft 24 is formed through relatively soft, deformable bone, as the ends of the flexible member 38 are pulled, the fixation member 28 is reduced toward the graft 24, e.g. bone graft, such that the post 30 is inserted into the passage 26, forming a slip fit with the passage 26. In embodiments, once fully-inserted, the post 30 is long enough to extend completely through the graft 24 and at least partially through the hole 10 of the glenoid 12. Once the graft 24 is in the preferred position, a surgical knot, which is the anterior fixation member 28 in some embodiments, is tied in the flexible member 38, fixing the graft 24 into place. The ends of the flexible member 38 may then be trimmed.

In embodiments, the fixation member 22, 28 has a generally circular body having a first surface, which may be flat or convex, for facing away from bone, and an opposite concave (or bowl-shaped) second surface, for facing bone. The fixation member 22, 28 further includes a post 30 fixedly coupled to a center of the body and extending perpendicular to the body. For example, a length of the post 30 may be about 35 mm and a width of the post may be about 2.5 mm. The fixation member 22, 28 also includes a length of flexible cable, which may comprise braided suture, coupled to the distal end of the post. A flexible member 38, such as a suture, may be threaded through the cable such that it forms a loop at the distal end of the cable.

In some embodiments, axially aligned hole(s) 10 are drilled through the patient's glenoid 12 and passage(s) 26 drilled through the patient's bone graft 24. A flexible member 38, e.g. a tension suture, is slidably coupled to the post 30, which may include an eyelet 36, of the fixation member 22, such that the distance between the fixation member 22 and an ancillary fastener 28 can be adjusted by pulling on the ends of the flexible member 38. The ends of the flexible member 38 are pulled through the passage(s) 26 in the bone graft 24 and the patient's glenoid 12, until the second surface of the fixation member 28 is positioned above a surface of the bone graft 24 and the ends of the flexible member 38 extend from the holes 10. As the ends of the flexible member 38 are pulled, the fixation member 28 is reduced toward the bone graft 24 such that the post 30 is inserted into the passage(s) 26. Once fully-inserted, the post 30 extends completely through the passage(s) 26 of the bone graft 24 and at least partially through the hole 10 of the glenoid 12. The flexible member 38 may then couple to the fixation member 22 or an ancillary fastener 28 of the fixation member 22. Once the bone graft 24 is in the preferred position, a surgical knot is tied in the flexible member 38 below the ancillary fastener 28, fixing the bone graft 24 into place. The ends of the flexible member 38 may then be trimmed.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method for suspension fixation of a graft or implant, the method comprising:
   drilling a hole through a glenoid from an anterior side of the glenoid via an anterior portal;

passing a pin having a first end and a second end pre-assembled to a first flexible member through the hole in the glenoid via the anterior portal and out past a posterior side of the glenoid such that both the first and second ends of the pin are spaced apart from a posterior surface of the glenoid on the posterior side;

securing the first flexible member to a second flexible member attached to a posterior fixation member;

retrieving the first flexible member anteriorly so as to pass the second flexible member through the hole in the glenoid and draw the posterior fixation member into contact with the posterior surface of the glenoid; and securing a graft or implant to an anterior surface of the glenoid via suspension fixation between the posterior fixation member and an anterior fixation member.

2. The method of claim 1, wherein the posterior fixation member comprises a first post, the anterior fixation member comprises a second post, and a diameter of the hole is substantially equal to a diameter of the first or second post.

3. The method of claim 1, wherein the pin further comprises an advancing end and a slot at the advancing end.

4. The method of claim 1, further comprising drilling a second hole to provide a second point of fixation.

5. The method of claim 1, further comprising tying a surgical knot in the second flexible member, wherein the second flexible member is a suture.

6. The method of claim 1, wherein the second flexible member is a suture loop.

7. The method of claim 1, wherein the first flexible member is a shuttle suture.

8. The method of claim 1, wherein the anterior fixation member is a knot.

* * * * *